(12) United States Patent
Kojima

(10) Patent No.: US 6,630,585 B2
(45) Date of Patent: Oct. 7, 2003

(54) METHOD FOR PURIFYING NUCLEIC ACIDS FROM FECES

(75) Inventor: Kouichi Kojima, Tokyo (JP)

(73) Assignee: Shimadzu Corporation, Kyoto (JP)

( * ) Notice: Subject to any disclaimer, the term of this patent is extended or adjusted under 35 U.S.C. 154(b) by 36 days.

(21) Appl. No.: 09/883,378

(22) Filed: Jun. 19, 2001

(65) Prior Publication Data

US 2002/0068292 A1 Jun. 6, 2002

(30) Foreign Application Priority Data

Jul. 26, 2000 (JP) ........................................ 2000-224870

(51) Int. Cl.⁷ ............................ C07H 21/04; C12Q 1/68
(52) U.S. Cl. ............................ 536/25.41; 435/4; 435/6; 528/44; 528/71; 536/23.1; 536/25.4
(58) Field of Search ........................... 435/4, 6; 528/44, 528/71; 536/23.1, 25.4, 25.41

(56) References Cited

U.S. PATENT DOCUMENTS 5,654,179 A  *  8/1997  Lin ............................ 435/91.2

* cited by examiner

*Primary Examiner*—David Guzo
(74) *Attorney, Agent, or Firm*—Rader, Fishman & Grauer PLLC

(57) ABSTRACT

An object of the present invention is to provide a method capable of removing contaminants other than nucleic acids derived from feces at high efficiency, and thereby obtaining nucleic acids with high purity, although it is difficult to purify nucleic acids in high purity from feces.

In the present invention, a feces sample is purified using a quaternary ammonium salt such as, for example, hexadecyltrimethylammonium bromide.

18 Claims, 3 Drawing Sheets

METHOD FOR PURIFYING NUCLEIC ACIDS FROM FECES

BACKGROUND OF THE INVENTION

1. Field of the Invention

The present invention relates to a method for purifying nucleic acids to obtain nucleic acids that are used as a sample in the case that various procedures are conducted using nucleic acids.

2. Description of the Related Art

As a method for purifying nucleic acids, a method comprising breaking down proteins by means of enzymes such as proteinases, and then removing the decomposed proteins and components of fat-soluble contaminants by conducting a phenol-chloroform extraction, has been generally used.

Besides the above method, a method comprising allowing nucleic acids to be absorbed on glass beads and removing components other than nucleic acids, a method for purifying nucleic acids by filtering only nucleic acids using a filter, and others, have been developed.

However, nucleic acids with high purity cannot be obtained from feces by the above-mentioned methods. By the method conducting the phenol-chloroform extraction after treating the feces with the enzymes using the proteinases, contaminants other than the fat-soluble contaminants cannot be removed. By the method comprising allowing the nucleic acids to be absorbed on the glass beads, contaminants in the feces inhibit absorption of the nucleic acids on the glass beads. By the method using the filer, filtration cannot be accomplished due to clogging of the filter with contaminants in the feces.

Indeed, after a process for purifying nucleic acids was performed by treating feces as a sample with enzymes using proteinases followed by conducting the phenol-chloroform extraction, precipitates of the nucleic acids were obtained by an ethanol precipitation method. As a result, the precipitates were yellowish or brownish. This result indicates that contaminants in the feces are not removed and purification of the nucleic acids is not accomplished in high purity.

SUMMARY OF THE INVENTION

An object of the present invention is to provide a method capable of removing contaminants other than nucleic acids derived from feces at high efficiency and thereby obtaining nucleic acids with high purity, although it is difficult to purify the nucleic acids in high purity from feces.

In order to solve the subjects described above, the present invention is a method for purifying nucleic acids from feces, wherein a feces sample is purified using a quaternary ammonium salt.

The present invention is the method for purifying nucleic acids, wherein an organic solvent is also used.

The present invention is the method for purifying nucleic acids, wherein the quaternary ammonium salt selected from the group consisting of hexadecyltrimethylammonium bromide, hexadecylpyridinium chloride, hexadimethrine bromide, hexafluorenium bromide and methylthiazolium bromide is used as the quaternary ammonium salt.

The present invention is the method for purifying nucleic acids, wherein the quaternary ammonium salt is used by being dissolved into water or a pH buffer solution.

Further, the present invention is the method for purifying nucleic acids, wherein at least one organic solvent selected from the group consisting of chloroform, carbon tetrachloride, phenol, benzene, ethers, acetone and alcohols is used as the organic solvent.

According to the present invention, nucleic acids with high purity can be obtained from feces, although it is difficult to obtain purified nucleic acids from the feces.

DETAILED DESCRIPTION OF THE INVENTION

Figure 1:
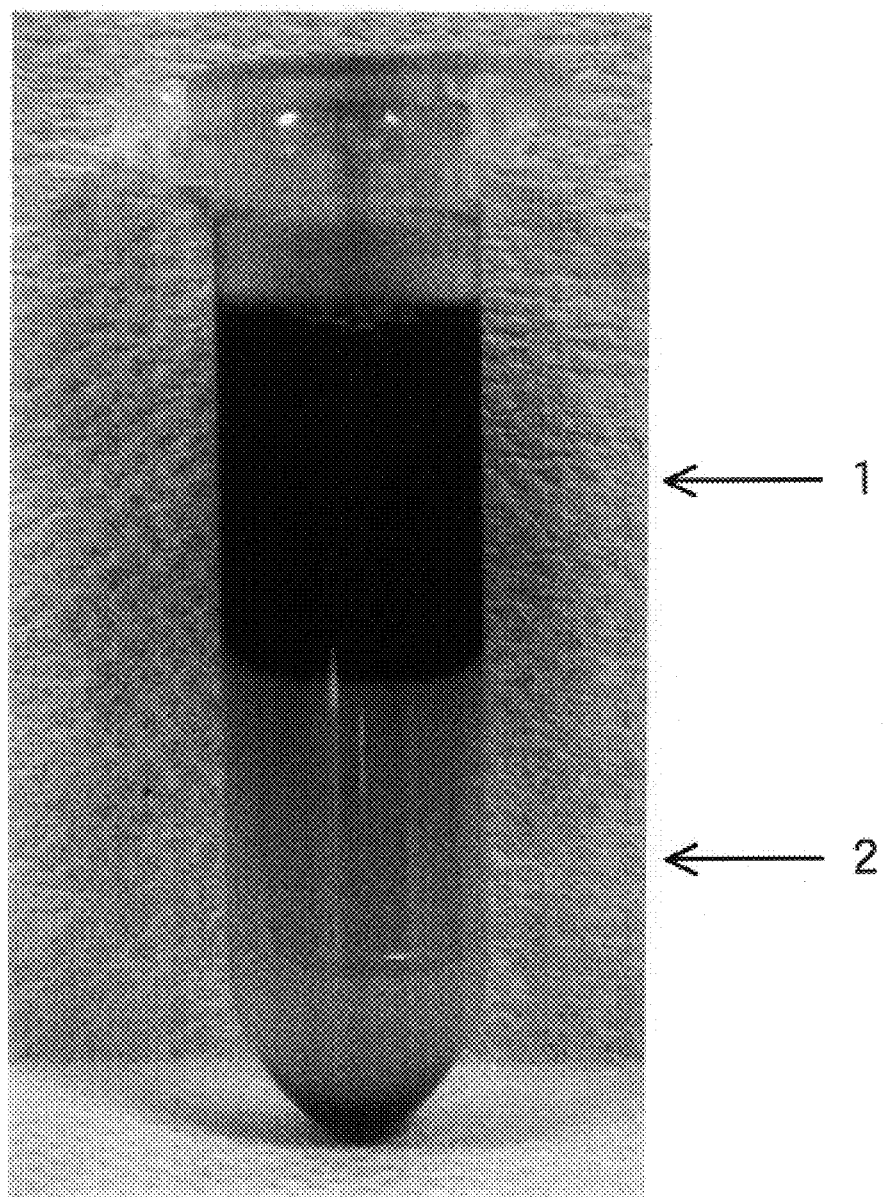
FIG. 1 shows a state of a feces sample in a tube before purification.

The present invention is a method for purifying nucleic acids, wherein a feces sample is purified using a quaternary ammonium salt.

Here, the quaternary ammonium salt includes, but not limited to, hexadecyltrimethylammonium bromide, hexadecylpyridinium chloride, hexadimethrine bromide, hexafluorenium bromide, methylthiazolium bromide and others. A concentration of the quaternary ammonium salt is normally in a range of 0.01% to 30% by weight, and preferably in a range of 0.1% to 5% by weight, with respect to water or a pH buffer solution. In the case that the concentration of the quaternary ammonium salt is lower than 0.01% by weight, purification effects cannot be available. In the case that the concentration of the quaternary ammonium salt is higher than 30% by weight, the quaternary ammonium salt tends to precipitate.

As a temperature condition, it is preferable to add the quaternary ammonium salt after heating a liquid containing feces at 40° C. to 100° C. As a means for heating, for example, a method comprising after allowing the sample to be suspended in a liquid, transferring the suspension to a plastic tube and heating the suspension using a heating block, may be mentioned, although the method is not so limited. For example, the heating may be conducted by transferring the suspension to a beaker followed by heating by means of a burner or the like.

As feces, feces derived from a human, a livestock, an insect or the like may be mentioned, although they are not so limited. Namely, feces derived from all animals may be applied.

Besides, an organic solvent may be used together with the quaternary ammonium salt. As the organic solvent, for example, chloroform, carbon tetrachloride, phenol, benzene, ethers, acetone and/or alcohols may be used, although they are not so limited.

In the present invention, as a process for using reagents described above, nucleic acids can be purified by the process comprising the steps of allowing feces to be suspended in water or a pH buffer solution, adding the quaternary ammonium salt thereto followed by stirring the resulted mixture, and then adding the organic solvent thereto followed by stirring the resulted mixture and centrifuging it. However, the process is not limited to the above-mentioned process, and the quaternary ammonium salt and the organic solvent may be added simultaneously. Further, the process may be conducted by preparing a quaternary ammonium salt-including suspension in which a feces sample is suspended in water containing the quaternary ammonium salt or in the pH buffer solution containing the quaternary ammonium salt, and adding the organic solvent thereto. Furthermore, the process may be conducted by preparing a liquid for nucleic acids purification comprising water or the pH buffer solution, the quaternary ammonium salt and the organic solvent in advance, and adding the feces sample into the liquid for nucleic acids purification. As the pH buffer solution in which feces are suspended, for example, a phosphate buffer, a TRIS buffer, an acetate buffer or the like may be used, although they are not so limited.

In the present invention, the term "nucleic acids" mean both DNA and RNA. In the present invention, nucleic acids of bacteria, viruses and protozoa that are present in feces derived from animals can be obtained. Particularly, in the present invention, nucleic acids of bacteria, viruses and protozoa that cause infectious diseases and are present in the feces derived from the animals, nucleic acids of variant cells such as tumor cells present in the feces derived from the animals, or the like, can be obtained.

EXAMPLES

The present invention is further described in the following examples which are not intended to restrict the invention.

Experimental Example 1

In this example, bovine feces were used as a sample to purify nucleic acids of enterobacteria contained in the feces.

In a tube, 1 g of the bovine feces were added into 9 ml of a phosphate buffer solution, and the resulted mixture was stirred to obtain a feces suspension. The feces suspension was let stand for 3 minutes to allow solid components contained in the feces to be precipitated, and a supernatant of the feces suspension was obtained.

In order to extract the nucleic acids into a solution by destroying cells of the enterobacteria, the above-mentioned supernatant of the feces suspension was heated at 100° C. for 5 minutes.

As a quaternary ammonium salt, hexadecyltrimethylammonium bromide was added into 1 ml of the heated supernatant to attain a concentration of 1% by weight, and after stirring the mixture 1 ml of chloroform was added thereto as an organic solvent. A state of the sample in the tube at the moment is indicated in FIG. 1. As it can be seen from FIG. 1, an aqueous layer (an upper layer) 1 containing the nucleic acids was intensively colored due to contaminants contained in the feces. On the other hand, an organic layer (a lower layer) 2 was clear.

Figure 2:
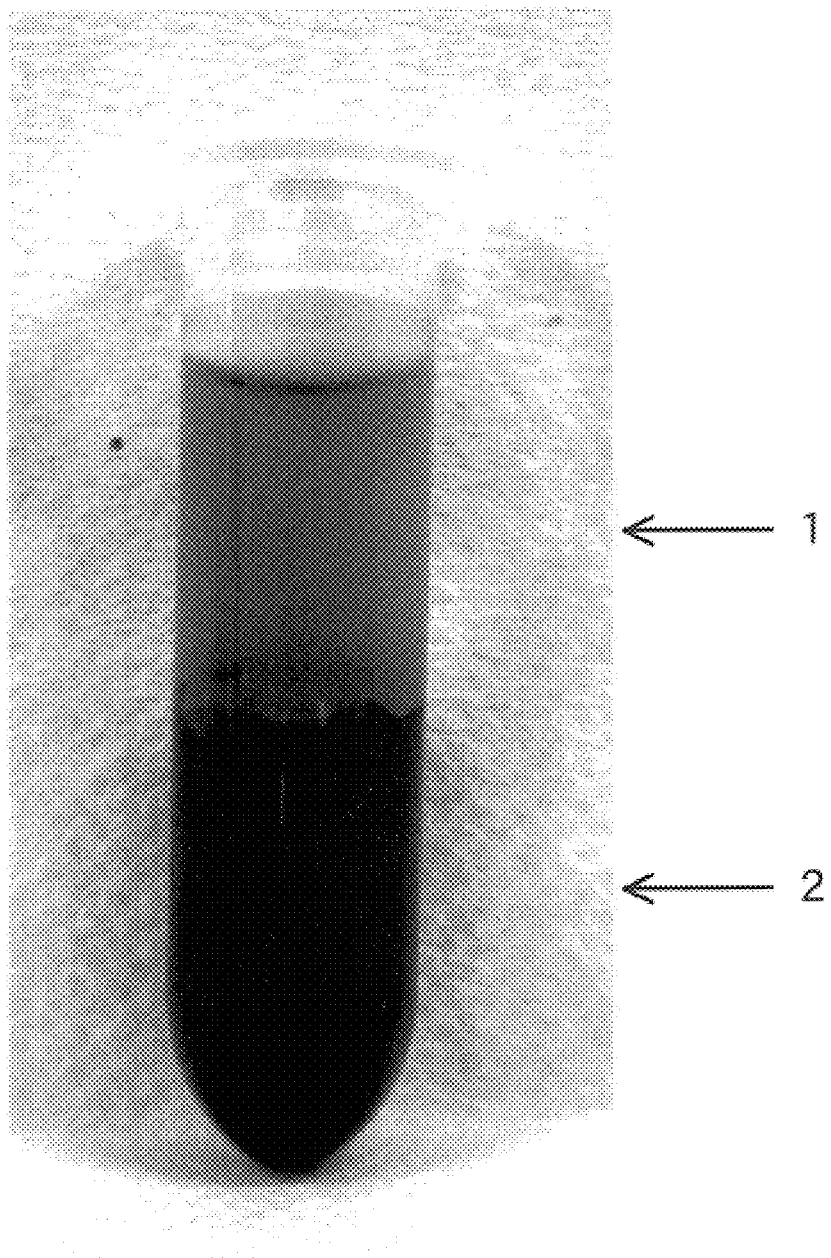
FIG. 2 shows a state of the feces sample in the tube after purification.

After stirring the mixture that was in the state illustrated in FIG. 1, the stirred mixture was centrifuged at a centrifugal force of 10,000 G for 5 minutes. A state of the sample in the tube at the moment is indicated in FIG. 2. As it can be seen from FIG. 2, the contaminants contained in the feces were transferred from the aqueous layer 1 to the organic layer 2 so that the aqueous layer 1 became clear and the organic layer 2 was colored. This result indicates that the contaminants contained in the feces were removed from the aqueous layer containing the nucleic acids, and thereby nucleic acids were purified.

The aforesaid aqueous layer 1 that had become clear was transferred to another new tube, and with respect to the aqueous layer transferred, the 1/10 volume of 3M sodium acetate solution and the 3-fold volume of ethanol were added thereto. After centrifuging the resulted mixture, the nucleic acids of the enterobacteria in the feces were obtained as a pellet (an ethanol precipitation of the nucleic acids). This pellet was white, and it was found that the nucleic acids were purified in high purity.

Experimental Example 2

In this example, bovine feces in which the bovine was infected with Johne's disease were used as a sample to purify nucleic acids of Johne's bacteria contained in the feces.

Reactions were conducted using nucleic acids purified by the method according to the present invention and nucleic acids purified by the conventional method as a template DNA for the PCR. And then, the degrees of each purification were compared by comparing yields of the products obtained by each reaction.

As the method according to the present invention, purified nucleic acids were obtained from the feces derived from the bovine infected with Johne's disease by the same method as in the Experimental Example 1.

As the conventional method, purification of nucleic acids from the feces derived from the bovine infected with Johne's disease was conducted by enzymatic treatment using proteinases followed by the phenol-chloroform extraction.

The nucleic acids purified by the method according to the present invention and the nucleic acids purified by the conventional method were subjected to a reaction system for a PCR that can amplify a sequence of nucleic acids of IS900, a specific gene in the Johne's bacteria. Sequences of primers used for the PCR were described below.

```
5' GATCGGAACGTCGGCTGGTCAGG 3'    SEQ ID. NO. 1

5' ACGACGACGCGCAGCGATTGCTCT 3'   SEQ ID. NO. 2
```

Taq polymerase was used as an enzyme. A temperature condition for the reaction was 40 cycles each of which consists 97° C. for 30 seconds followed by 65° C. for 30 seconds followed by 72° C. for 30 seconds.

Figure 3:
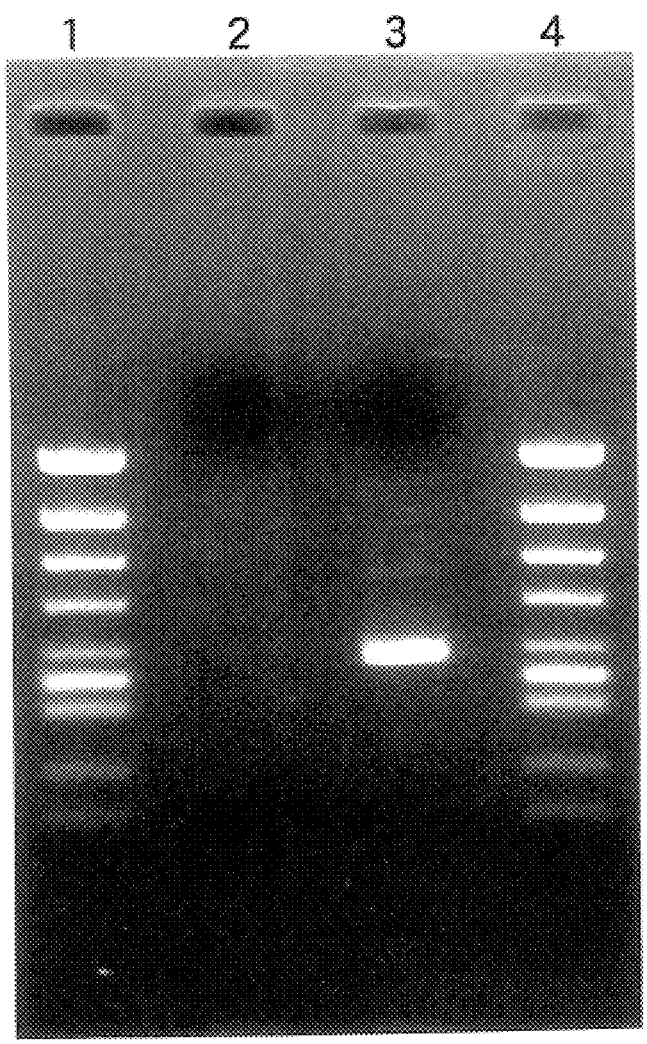
FIG. 3 shows the results of an agarose gel electrophoresis performed for detecting PCR products.

Products by the PCR described above were detected by means of an electrophoresis using an agarose gel. The results of the electrophoresis were shown in FIG. 3. In FIG. 3, lanes 1 and 4 indicate an electrophoretogram of molecular weight markers; a lane 3 indicates an electrophoretogram of the products by the PCR using the nucleic acids purified by the method according to the present invention as a template; a lane 2 indicates an electrophoretogram of the products by the PCR using the nucleic acids purified by the conventional method as a template.

It can be seen from FIG. 3 that intended products were detected from the PCR products using the nucleic acids purified by the method according to the present invention; however, no product was detected from the PCR products using the nucleic acids purified by the conventional method. This difference was caused by that the PCR was inhibited due to contaminants contained in the feces that were not sufficiently removed by the conventional method. From this experiment, it was demonstrated that nucleic acids could be purified from feces in sufficient purity for the PCR by the method according to the present invention.

What is claimed is:

1. A method for purifying nucleic acids from feces, which comprises:
   separating nucleic acids from contaminants in said feces sample, wherein said feces sample is in the presence of a quaternary ammonium sample.

2. The method for purifying nucleic acids according to claim 1, wherein an organic solvent is also used.

3. The method for purifying nucleic acids according to claim 1, wherein the quaternary ammonium salt selected from the group consisting of hexadecyltrimethylammonium bromide, hexadecylpyridinium chloride, hexadimethrine bromide, hexafluorenium bromide and methylthiazolium bromide is used as the quaternary ammonium salt.

4. The method for purifying nucleic acids according to claim 1, wherein the quaternary ammonium salt is used by being dissolved into water or a pH buffered solution.

5. The method for purifying nucleic acids according to claim 1, wherein the feces sample is derived from a human, a livestock or an insect.

6. The method for purifying nucleic acids according to claim 2, wherein at least one organic solvent selected from the group consisting of chloroform, carbon tetrachloride, phenol, benzene, ethers, acetone and alcohols is used as the organic solvent.

7. A method for purifying nucleic acids from feces, said method comprising the steps of:
   preparing a quaternary ammonium salt-including suspension in which a feces sample is suspended in water containing a quaternary ammonium salt or in a pH buffer solution containing the quaternary ammonium salt; and
   adding an organic solvent into the quaternary ammonium salt-including suspension.

8. The method for purifying nucleic acid according to claim 7 comprising the additional steps of:
   stirring the quaternary ammonium salt-including suspension added with the organic solvent to obtain a stirred mixture; and
   centrifuging the stirred mixture.

9. The method for purifying nucleic acids according to claim 7, wherein a concentration of the quaternary ammonium salt is 0.01 to 30% by weight with respect to the water or the pH buffer solution.

10. The method for purifying nucleic acids according to claim 7, wherein a concentration of the quaternary ammonium salt is 0.1 to 5% by weight with respect to the water or the pH buffer solution.

11. A method for purifying nucleic acids from feces, said method comprising the steps of:
   adding a feces sample into water or a pH buffer solution to prepare a feces suspension;
   adding a quaternary ammonium salt into the feces suspension to prepare a quaternary ammonium salt-including suspension; and then
   adding an organic solvent into the quaternary ammonium salt-including suspension.

12. The method for purifying nucleic acids according to claim 11 comprising the steps of:
   allowing the feces suspension to form a supernatant of the feces suspension; and then
   adding the quaternary ammonium salt into the supernatant of the feces suspension.

13. The method for purifying nucleic acids according to claim 11 comprising the additional steps of:
   stirring the quaternary ammonium salt-including suspension added with the organic solvent to obtain a stirred mixture; and
   centrifuging the stirred mixture.

14. The method for purifying nucleic acids according to claim 11 comprising adding the quaternary ammonium salt at a concentration of 0.01 to 30% by weight.

15. The method for purifying nucleic acids according to claim 11 comprising adding the quaternary ammonium salt at a concentration of 0.1 to 5% by weight.

16. The method for purifying nucleic acids according to claim 11 comprising the steps of:
   heating the feces suspension at a temperature of 40 to 100° C. before adding the quaternary ammonium salt into the feces suspension; and then adding the quaternary ammonium salt into the feces suspension.

17. A method for purifying nucleic acids from feces, said method comprising the steps of:

preparing a liquid for nucleic acids purification comprising water or a pH buffer solution, a quaternary ammonium salt and an organic solvent; and adding a feces sample into the liquid for nucleic acids purification.

18. The method for purifying nucleic acids according to claim 17 comprising the additional steps of:

stirring the liquid for nucleic acids purification added with the feces sample to obtain a stirred mixture; and centrifuging the stirred mixture.

* * * * *

SEQUENCE LISTING

<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: A sequence of Primers used for the PCR

<400> SEQUENCE: 1
gatcggaacg tcggctggtc agg                                    23

<210> SEQ ID NO 2
<211> LENGTH: 24
<212> TYPE: DNA
<213> ORGANISM: Artificial Sequence
<220> FEATURE:
<223> OTHER INFORMATION: A sequence of Primers for the PCR

<400> SEQUENCE: 2
acgacgacgc gcagcgattg ctct                                   24